US008540908B2

(12) United States Patent
Chen et al.

(10) Patent No.: US 8,540,908 B2
(45) Date of Patent: Sep. 24, 2013

(54) METHOD OF PREPARING NANO-DISPERSED HIGH-ALL-TRANS-CAROTENOID MICROCAPSULES

(75) Inventors: Zhirong Chen, Hangzhou (CN); Jianfeng Chen, Beijing (CN); Hong Yin, Hangzhou (CN); Hong Zhao, Beijing (CN); Dan Qiu, Hangzhou (CN); Lifang Shi, Shaoxing (CN); Jiandong Li, Shaoxing (CN); Guangwen Chu, Beijing (CN); Lei Shao, Beijing (CN)

(73) Assignees: Zhejiang NHU Company Ltd., Shaoxing, Zhejiang Province (CN); Zhejiang University, Hangzhou, Zhejiang Province (CN); Beijing University of Chemical Technology, Beijing (CN)

( * ) Notice: Subject to any disclaimer, the term of this patent is extended or adjusted under 35 U.S.C. 154(b) by 182 days.

(21) Appl. No.: 13/259,291

(22) PCT Filed: Mar. 18, 2010

(86) PCT No.: PCT/CN2010/071121
§ 371 (c)(1),
(2), (4) Date: Sep. 23, 2011

(87) PCT Pub. No.: WO2010/111912
PCT Pub. Date: Oct. 7, 2010

(65) Prior Publication Data
US 2012/0018912 A1 Jan. 26, 2012

(30) Foreign Application Priority Data
Mar. 30, 2009 (CN) .......................... 2009 1 0097063

(51) Int. Cl.
*B01J 13/04* (2006.01)
(52) U.S. Cl.
USPC ............................ 264/4.1; 424/489; 424/490
(58) Field of Classification Search
None
See application file for complete search history.

(56) References Cited

U.S. PATENT DOCUMENTS

| 3,998,753 A | 12/1976 | Antoshkiw et al. | |
|---|---|---|---|
| 4,522,743 A | 6/1985 | Horn et al. | |
| 5,780,056 A * | 7/1998 | Akamatsu et al. | 424/464 |
| 6,663,900 B2 * | 12/2003 | DeFreitas et al. | 424/492 |
| 2005/0037115 A1 | 2/2005 | Fullmer et al. | |
| 2007/0269526 A1* | 11/2007 | Bos et al. | 424/502 |
| 2008/0181960 A1* | 7/2008 | Doney | 424/489 |

FOREIGN PATENT DOCUMENTS

| CN | 1836652 A | 9/2006 |
|---|---|---|
| CN | 101016259 A | 8/2007 |
| EP | 0065193 A2 | 11/1982 |
| WO | WO91/06292 A1 | 5/1991 |
| WO | WO94/19411 | 9/1994 |
| WO | WO03/017785 A1 | 3/2003 |

OTHER PUBLICATIONS

Henelyta S. Ribeitro et al., Preparation of nanodispersions containing beta-carotene by solvent displacement method, Food Hydrocolloids 22 (2008) pp. 12-17.
Xiaoyun Pan et al., Simultaneous nanoparticle formation nad encapsulation driven by hydrophobic interaction,Journal of Colloid and Interface Science 315 (2007), pp. 456-463.
C. P. Tan & M. Nakajima, Beta-carotene nanodispersions: preparation, characterization and stability evaluation, Food Chemistry 92 (2005), pp. 661-671.

* cited by examiner

*Primary Examiner* — Mary F Theisen
(74) *Attorney, Agent, or Firm* — Jacobson Holman PLLC; Jiwen Chen

(57) ABSTRACT

A method of preparing nano-dispersed high-all-trans-carotenoid microcapsules is provided, comprising: preparing 10-20% carotenoid suspension by milling the high-all trans-carotenoid crystals with dichloromethane until the particle size thereof is in the range of 2-5 μm, then supplying the suspension together with preheated dichloromethane of another pass into a dissolving tank to obtain a solution of 0.5-2%; delivering the solution together with ethanol or isopropanol into a crystallization device having high gravity rotating packed bed simultaneously and continuously, and then into a wiped-film evaporator for desolvation until the solid content is 10-20%, then a transparent alcohol dispersion of carotenoid is obtained; mashing the alcohol dispersion together with an aqueous solution containing an antioxidant and protective colloid and spray drying to obtain nano-dispersed high-all-trans-carotenoid microcapsules. As the crystals are nano-dispersed and the content of trans-isomer is more than 90%, the carotenoid microcapsules of present inventions exhibit high bioavailability.

6 Claims, No Drawings

METHOD OF PREPARING NANO-DISPERSED HIGH-ALL-TRANS-CAROTENOID MICROCAPSULES

This is a U.S. national stage application of PCT Application No. PCT/CN2010/071121 under 35 U.S.C. 371, filed Mar. 18, 2010 and published in Chinese, claiming the priority benefit of Chinese Application No. 200910097063.2, filed Mar. 30, 2009, which is hereby incorporated by reference.

TECHNICAL FIELD

The present invention relates generally to a method of preparing carotenoid microcapsules and more specifically, to a method of preparing nano-dispersed high-all-trans-carotenoid microcapsules.

BACKGROUND OF THE ART

Carotenoids broadly exist in the nature. They include β-carotene, astaxanthin, canthaxanthin and lycopene. These substances are essential coloring agents used in industries such as food, cosmetics, animal feed stuffs and pharmaceutical industry. In addition, some of them are precursors of vitamin A. Carotenoids are substances which are insoluble in water and are almost insoluble in oil as well. Moreover, carotenoids are substances which are sensitive to heat and oxygen. Therefore, carotenoids are difficult to be absorbed by animals in the form of crystalline coarse particles. Either used in food or other areas, carotenoids in general need to be fine particles and require protective colloid to prevent oxidation. For the purpose of coloration, carotenoids are expected to be improved in bioavailability after being made into preparation to improve the effect of coloration, reduce the amount and minimize the losses in use.

Carotenoids are often made into water-dispersible preparation in using. For this purpose, some literatures have reported various methods of such preparations.

WO091/06292 and WO94/19411 described a method wherein β-carotene is ground into particles with the particle size of 2-10 μm using colloid mill and then is dried to be water-dispersible carotenoid powders. While the grinding efficiency is low, the power consumption is obvious and it is difficult to make the particle size of carotenoids less than 1 μm.

U.S. Pat. No. 3,998,753 described a kind of preparation method of water-dispersible carotenoids with a granularity of less than 1 μm. In this method, carotenoids and other additives are firstly mixed to form an organic solvent solution, which is added into the aqueous solution containing gelatin, dispersant and stabilizer, then the system is made into an emulsion through high speed shear; finally organic solvents are removed and required powders are obtained after spray drying.

In EP-0065193 (or U.S. Pat. No. 4,522,743) recorded a preparation method of water-dispersible carotenoid powders. First, carotenoids are dissolved in a volatile water-miscible solvent in 10 seconds at 50-200° C. and rapidly mixed with the aqueous solution containing protective colloid at 0-50° C., so carotenoids with the particle size of less than 0.5 μm are dispersed in the protective colloid, then carotenoid powders can be obtained after removing solvents and drying. The process requires high pressure (3.0-6.0 MPa) and high temperature (170-200° C.). This process has strict requirements for equipment and is difficult to operate and control.

In the above-mentioned methods using solvents or high temperature solvents, it is necessary to remove a large volume of solvents from the protective colloid system. The process takes a long time and thorough removal is not easy. The system will easily blister when being heated and precipitated in the presence of protective colloid, with a very low efficiency of precipitation. It is difficult to control the particle size and the content of trans isomer of required carotenoid powders.

Because of the problems existing in the above patents, the applicant of the present invention applied for a preparation method of water-dispersible carotenoid powders in 2005 (the publication number of the patent is CN1836652A). In the method, coarse carotenoid crystals are firstly dissolved in halogenated hydrocarbon or esters which contain antioxidants and emulsifiers. The obtained solution is sprayed into high speed mixing ethanol or isopropanol to separate out carotenoids as amorphous powders with a particle size of less than 2 μm. The precipitated carotenoids are filtered through a filter film or a sintered filter rod. The filtered cake is washed by ethanol or isopropanol and drained. The filter cake is then added into the aqueous solution containing protective colloid, stirred, homogenized and emulsified. The residual solvents are removed to prepare an aqueous dispersion. Then, the dispersion is sprayed for pelletization. Finally water-dispersible carotenoid preparations can be obtained after fluidization desiccation. The method has the advantages of less residual solvents, rapid removal and high efficiency while the particle size of carotenoid crystal powders is 0.7-0.9 μm and the content of all-trans-isomer is less than 85%.

To increase the content of all-trans-isomer in carotenoid powders, we also proposed that combined antioxidants can be added to improve the double-solvent method (the publication number of the patent is CN101016259A). However, the particle size of carotenoid crystal powders is still 0.7-0.9 μm. The bioavailability still needs improvement.

In US2005/0037115, a preparation method of nano-dispersion of carotenoids is described. Carotenoids are dissolved in a fatty acid ester solvent and the solution is added to an aqueous phase containing dispersant. A nano-dispersion liquid of carotenoids can be obtained after the solvent is evaporated. The solubility of carotenoids is very low in esters, thus, only products with the content of less than 0.5% can be obtained.

Henelyta S. Ribeitro et al. (Food Hydrocolloids 22 (2008) 12-17) adopt acetone as a solvent and PLA or PLGA as a polymer. The polymer and β-carotene are firstly dissolved in acetone. Then the solution is added into the aqueous solution containing gelatin and Tween-20. Nano-β-carotene dispersion is made by using solvent-replacement method. Because the solubility of β-carotene in acetone is very small, the content of β-carotene dispersion is quite low.

Xiaoyun Pan et al. (Journal of Colloid and Interface Science 315 (2007) 456-463) adopt absolute ethyl alcohol as a solvent to dissolve or disperse β-carotene. The solution is added into the aqueous solution containing graft casein. Nano-β-carotene dispersion is made by using solvent-replacement method. Similarly, the solubility of β-carotene in alcohol is very small and the content of β-carotene dispersion is quite low.

C. P. Tan and M. Nakajima (Food Chemistry 92 (2005) 661-671) reported that β-carotene is dissolved in hexane and added to the aqueous solution containing Tween 20. The solution is desolventized in a fluidized bed after pre-emulsion and homogenization to form nano-dispersed system of β-carotene.

The nanocrystallization methods mentioned above have all adopted the solvents in which the solubility of β-carotene is very low, so it is difficult to obtain nano-dispersed β-carotene microcapsules with industrial value.

DISCLOSURE OF THE INVENTION

Technical Problem

The present invention aims to provide a method of preparing nano-dispersed high-all-trans-carotenoid microcapsules with not only high content of all-trans-isomers but also nano-dispersed crystals.

Technical Solution

The method of preparing nano-dispersed high-all-trans-carotenoid microcapsules comprises the following steps:

1) milling the crystallized carotenoid with more than 98% of all-trans crystallized carotenoid and solvent dichloromethane until the particle size thereof is in the range of 2-5 μm, resulting in 10-20% carotenoid suspension;

2) continuously supplying the carotenoid suspension to a dissolving tank, while supplying dichloromethane after being preheated to 45-50° C. by a heat exchanger to the dissolving tank, maintaining the pressure at 0.2-0.3 MPa and the temperature at 35-40° C. in the dissolving tank, and with materials retention time of 4-12 minutes, to dissolve the crystallized carotenoid completely, resulting in dichloromethane solution with 0.5-2.0% of carotenoids;

3) continuously supplying dichloromethane solution with 0.5-2.0% of carotenoids to a crystallization device having a high gravity rotating packed bed and a liquid distributor; and also adding ethanol or isopropanol, with the weight of 5-10 times of dichloromethane solution, into the crystallization device; then precipitating carotenoid to be nano-crystal and obtaining a clear carotenoid dispersion;

4) continuously desolventizing the clear carotenoid dispersion under a reduced pressure in a wiped-film evaporator and obtaining alcohol dispersion with 10-20% of nano-dispersed carotenoid;

5) mixing the alcohol dispersion with nano-dispersed carotenoid and the aqueous solution of antioxidant and protective colloid, and beating in another high gravity rotating packed bed; then spray drying the mixture to obtain nano-dispersed high-all-trans-carotenoid microcapsules.

The carotenoids refer to astaxanthin, canthaxanthin, β-carotene or lycopene. The dissolving tank is a multi-layer agitator with the ratio of height to diameter of 3-4, and it is divided into 3-4 segments in each of which there is a stirrer; the materials are fed from the bottom of the tank and poured from the top of the tank. The high gravity rotating packed bed has wire mesh packing and liquid distributor, and the rotate speed is 1000-3000 r/min. The antioxidant is vitamin C, sodium L-ascorbate, isoascorbic acid or sodium D-isoascorbate. The protective colloid is gelatin, fish gelatin or modified starch.

The essence of the present invention is to quickly dissolve crystallized carotenoid after being milled in solvents and then to form nano-dispersed carotenoid dispersion under supergravity in a crystallization device having a high gravity rotating packed bed, then to rapidly desolventize the carotenoid dispersion in a wiped-film evaporator, to beat in a high gravity rotating packed bed and immediately to spray dry, to obtain nano-dispersed carotenoid microcapsules. Thus, the time of being heated for carotenoids is very short in the process of preparation and very high content of all-trans-isomer can be maintained.

In the nano-dispersed high-all-trans-carotenoid microcapsules based on the present invention, $D_{95}$ of carotenoid crystal is less than 300 nm and the content of all-trans-isomer is more than 90%.

Advantageous Results

The present invention is advantageous because there is no requirement for high-pressure equipment, relatively simple operation and control, continuous production, less residual solvents in products as well as high bioavailability.

BEST MODE OF THE INVENTION

Example 1

10 kg of crystallized astaxanthin (the content of all-trans is 98.6%) and 40 kg of dichloromethane were milled together in a sand mill, resulting in 20% astaxanthin suspension with the astaxanthin particle size of 5 μm. 1 kg of isoascorbic acid and 85 kg of gelatin were dissolved in 200 kg of water and the solution was cooled to 40° C. for use.

Through a slurry pump, at the flow rate of 5 kg/hour, the 20% astaxanthin suspension was supplied to the bottom of a dissolving tank with the volume of 5 L and the ratio of height to diameter of 3, the said dissolving tank having 3 agitating layers and being divided into 3 segments. Simultaneously, dichloromethane was preheated to 50° C. by a coil pre-heater and then was also supplied to the bottom of the dissolving tank at the flow rate of 95 kg/hour. The temperature was kept at 40° C. and the pressure was kept at 0.3 MPa in the dissolving tank. The analysis for sampling after the retention time of about 4 minutes indicated that the crystallized astaxanthin was completely dissolved, resulting in dichloromethane solution with 1% by concentration of astaxanthin. The dichloromethane solution with 1% by concentration of astaxanthin was supplied to a crystallization device with a high gravity rotating packed bed having a liquid distributor and wire mesh packing. Simultaneously, ethanol was supplied to the crystallization device with a high gravity rotating packed bed at the flow rate of 500 kg/hour. The rotation rate was kept at 1500 rev/min. Nano-dispersed astaxanthin dispersion with the flow rate of 600 kg/hour was obtained at the outlet of the crystallization device with a high gravity rotating packed bed. The dispersion was desolventized under a reduced pressure in a falling film evaporator to remove most of the solvents and astaxanthin ethanol dispersion with the flow rate of 10 kg/hour (the solid content is about 10%) was obtained. The above-mentioned astaxanthin ethanol dispersion was fed into another high gravity rotating packed bed beater at the rate of 10 kg/hour by a pump. At the same time, the mixed aqueous solution of gelatin at the flow rate of 28 kg/hour was fed into the high gravity rotating packed bed beater. Then a slurry with the flow rate of about 38 kg/hour was obtained. The slurry was supplied into a spray dryer for drying and astaxanthin microcapsules at the flow rate of about 9.5 kg/hour were obtained. Thus, 95 kg of astaxanthin microcapsules were obtained in 10 hours. The result of the test showed that the content of astaxanthin in the microcapsules was 10.3% and the content of all-trans-isomer was 91.7%. The result of particle-size analysis showed that $D_{95}$ of crystallized astaxanthin in the products was 220 nm.

Implementation Modes for the Invention

Example 2

10 kg of crystallized canthaxanthin (the content of all-trans is 98.8%) and 90 kg of dichloromethane were milled together in a sand mill, resulting in 10% canthaxanthin suspension with the canthaxanthin particle size of 2 μm. 1 kg of sodium D-isoascorbate and 85 kg of fish gelatin were dissolved in 200 kg of water and the solution was cooled to 40° C. for use. Through a slurry pump, at the flow rate of 10 kg/hour, the 10% canthaxanthin suspension was supplied to the bottom of a dissolving tank with the volume of 4 L and the ratio of height to diameter of 4, the said dissolving tank having 4 agitating layers and being divided into 4 segments. Simultaneously, dichloromethane was preheated to 45° C. by a coil pre-heater and then was also supplied to the bottom of the dissolving tank at the flow rate of 40 kg/hour. The temperature was kept at 35° C. and the pressure was kept at 0.2 MPa in the dissolving tank. The analysis for sampling after the retention time of about 12 minutes indicated that the crystallized canthaxanthin was completely dissolved, resulting in dichloromethane solution with 2% by concentration of canthaxanthin. The dichloromethane solution with 2% by concentration of canthaxanthin was supplied to a crystallization device with a high gravity rotating packed bed having a liquid distributor and wire mesh packing Simultaneously, ethanol was supplied to the crystallization device with a high gravity rotating packed bed at the flow rate of 500 kg/hour. The rotation rate was kept at 1000 rev/min. Nano-dispersed canthaxanthin dispersion with the flow rate of 550 kg/hour was obtained at the outlet of the crystallization device with a high gravity rotating packed bed. The dispersion was desolventized under a reduced pressure in a falling film evaporator to remove most of the solvents and canthaxanthin ethanol dispersion with the flow rate of 5 kg/hour (the solid content is about 20%) was obtained. The above-mentioned canthaxanthin ethanol dispersion was fed into another high gravity rotating packed bed beater at the rate of 5 kg/hour by a pump. At the same time, the mixed aqueous solution of gelatin at the flow rate of 28 kg/hour was fed into the high gravity rotating packed bed beater. Then a slurry with the flow rate of about 33 kg/hour was obtained. The slurry was supplied into a spray dryer for drying and canthaxanthin microcapsules at the flow rate of about 9.6 kg/hour were obtained. Thus, 96 kg of canthaxanthin microcapsules were obtained in 10 hours. The result of the test showed that the content of canthaxanthin in the microcapsules was 10.2% and the content of all-trans-isomer was 92.8%. The result of particle-size analysis showed that $D_{95}$ of crystallized canthaxanthin in the products was 230 nm.

Example 3

10 kg of crystallized β-carotene (the content of all-trans is 98.4%) and 70 kg of dichloromethane were milled together in a sand mill, resulting in 12.5% β-carotene suspension with the β-carotene particle size of 3 μm. 0.5 kg of vitamin C, 0.5 kg of sodium L-ascorbate and 85 kg of modified starch were dissolved in 200 kg of water and the solution was cooled to 40° C. for use.

Through a slurry pump, at the flow rate of 8 kg/hour, the 12.5% β-carotene suspension was supplied to the bottom of a dissolving tank with the volume of 4 L and the ratio of height to diameter of 4, the said dissolving tank having 4 agitating layers and being divided into 4 segments. Simultaneously, dichloromethane was preheated to 47° C. by a coil pre-heater and then was also supplied to the bottom of the dissolving tank at the flow rate of 192 kg/hour. The temperature was kept at 38° C. and the pressure was kept at 0.25 MPa in the dissolving tank. The analysis for sampling after the retention time of about 5.4 minutes indicated that the crystallized β-carotene was completely dissolved, resulting in dichloromethane solution with 0.5% by concentration of β-carotene. The dichloromethane solution with 0.5% by concentration of β-carotene was supplied to a crystallization device with a high gravity rotating packed bed having a liquid distributor and wire mesh packing Simultaneously, isopropanol was supplied to the crystallization device with a high gravity rotating packed bed at the flow rate of 1000 kg/hour. The rotation rate was kept at 3000 rev/min. Nano-dispersed β-carotene dispersion with the flow rate of 1200 kg/hour was obtained at the outlet of the crystallization device with a high gravity rotating packed bed. The dispersion was desolventized under a reduced pressure in a falling film evaporator to remove most of the solvents and β-carotene isopropanol dispersion with the flow rate of 7 kg/hour (the solid content is about 14.3%) was obtained. The above-mentioned β-carotene isopropanol dispersion was fed into another high gravity rotating packed bed beater at the rate of 7 kg/hour by a pump. At the same time, the mixed aqueous solution of gelatin at the flow rate of 28 kg/hour was fed into the high gravity rotating packed bed beater. Then a slurry with the flow rate of about 35 kg/hour was obtained. The slurry was supplied into a spray dryer for drying and β-carotene microcapsules at the flow rate of about 9.4 kg/hour were obtained. Thus, 94 kg of β-carotene microcapsules were obtained in 10 hours. The result of the test showed that the content of β-carotene in the microcapsules was 10.4% and the content of all-trans-isomer was 93.2%. The result of particle-size analysis showed that $D_{95}$ of crystallized β-carotene in the products was 205 nm.

Example 4

10 kg of crystallized lycopene (the content of all-trans is 98.6%) and 70 kg of dichloromethane were milled together in a sand mill, resulting in 12.5% lycopene suspension with the lycopene particle size of 4 μm. 0.5 kg of vitamin C, 0.5 kg of sodium L-ascorbate and 85 kg of modified starch were dissolved in 200 kg of water and the solution was cooled to 40° C. for use.

Through a slurry pump, at the flow rate of 8 kg/hour, the 12.5% lycopene suspension was supplied to the bottom of a dissolving tank with the volume of 4 L and the ratio of height to diameter of 4, the said dissolving tank having 4 agitating layers and being divided into 4 segments. Simultaneously, dichloromethane was preheated to 48° C. by a coil pre-heater and then was also supplied to the bottom of the dissolving tank at the flow rate of 192 kg/hour. The temperature was kept at 37° C. and the pressure was kept at 0.28 MPa in the dissolving tank. The analysis for sampling after the retention time of about 5.4 minutes indicated that the crystallized lycopene was completely dissolved, resulting in dichloromethane solution with 0.5% by concentration of lycopene. The dichloromethane solution with 0.5% by concentration of lycopene was supplied to a crystallization device with a high gravity rotating packed bed having a liquid distributor and wire mesh packing Simultaneously, isopropanol was supplied to the crystallization device with a high gravity rotating packed bed at the flow rate of 1000 kg/hour. The rotation rate was kept at 2000 rev/min. Nano-dispersed lycopene dispersion with the flow rate of 1200 kg/hour was obtained at the outlet of the crystallization device with a high gravity rotating packed bed. The dispersion was desolventized under a reduced pressure in a falling film evaporator to remove most of the solvents and lycopene isopropanol dispersion with the flow rate of 7 kg/hour (the solid content is about 14.3%) was obtained. The above-mentioned lycopene isopropanol dispersion was fed into another high gravity rotating packed bed beater at the rate of 7 kg/hour by a pump. At the same time, the mixed aqueous solution of gelatin at the flow rate of 28 kg/hour was fed into the high gravity rotating packed bed beater. Then a slurry with the flow rate of about 35 kg/hour was obtained. The slurry was supplied into a spray dryer for drying and lycopene microcapsules at the flow rate of about 9.4 kg/hour were obtained. Thus, 94 kg of lycopene microcapsules were obtained in 10 hours. The result of the test showed that the content of lycopene in the microcapsules was 10.3% and the content of all-trans-isomer was 92.5%. The result of particle-size analysis showed that $D_{95}$ of crystallized lycopene in the products was 210 nm.

INDUSTRIAL APPLICABILITY

The present invention is applicable to industrialized mass production.

The invention claimed is:

1. A method of preparing nano-dispersed high-all-trans-carotenoid microcapsules, which comprises of the steps of:
   1) milling crystallized carotenoid with more than 98% of all-trans and dichloromethane until particle size thereof is in the range of 2-5 μm, resulting in 10-20% carotenoid suspension;
   2) continuously supplying the carotenoid suspension to a dissolving tank, while supplying dichloromethane after being preheated to 45-50° C. by a heat exchanger to the dissolving tank, maintaining the pressure at 0.2-0.3 MPa and the temperature at 35-40° C. in the dissolving tank, and with materials retention time of 4-12 minutes, to dissolve the crystallized carotenoid completely, resulting in dichloromethane solution with 0.5-2.0% of carotenoids;
   3) continuously supplying dichloromethane solution with 0.5-2.0% of carotenoids to a crystallization device having a high gravity rotating packed bed and a liquid distributor; and also adding ethanol or isopropanol, with the weight of 5-10 times of dichloromethane solution, into the crystallization device; then precipitating carotenoid to be nano-crystal and obtaining a clear carotenoid dispersion;
   4) continuously desolventizing the clear carotenoid dispersion under a reduced pressure in a wiped-film evaporator and obtaining alcohol dispersion with 10-20% of nano-dispersed carotenoid;
   5) mixing the alcohol dispersion with nano-dispersed carotenoid and aqueous solution of antioxidant and protective colloid, and beating in another high gravity rotating packed bed; then spray drying the mixture to obtain nano-dispersed high-all-trans-carotenoid microcapsules.

2. The method of claim 1, wherein the carotenoids refer to astaxanthin, canthaxanthin, β-carotene or lycopene.

3. The method of claim 1, wherein the dissolving tank is a multi-layer agitator with the ratio of height to diameter of 3-4, and it is divided into 3-4 segments in each of which there is a stirrer; the materials are fed from a bottom of the tank and poured from a top of the tank.

4. The method of claim 1, wherein the high gravity rotating packed bed has wire mesh packing and liquid distributor, and rotate speed is 1000-3000 rev/min.

5. The method of claim 1, wherein the antioxidant is vitamin C, sodium L-ascorbate, isoascorbic acid or sodium D-isoascorbate.

6. The method of claim 1, wherein the protective colloid is gelatin, fish gelatin or modified starch.

* * * * *